(12) United States Patent
Prausnitz et al.

(10) Patent No.: US 6,503,231 B1
(45) Date of Patent: *Jan. 7, 2003

(54) MICRONEEDLE DEVICE FOR TRANSPORT OF MOLECULES ACROSS TISSUE

(75) Inventors: Mark R. Prausnitz, Atlanta, GA (US); Mark G. Allen, Atlanta, GA (US); Devin V. McAllister, Holley, NY (US); Sebastien Henry, Ay (FR)

(73) Assignee: Georgia Tech Research Corporation, Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/095,221

(22) Filed: Jun. 10, 1998

(51) Int. Cl.[7] .................................................. A61M 5/32
(52) U.S. Cl. ...................................... 604/272; 604/191
(58) Field of Search ............................. 935/53; 604/20, 604/22, 35, 46, 501, 506, 181, 183, 239, 261, 890.1, 272, 191, 186; 347/47; 29/890.01; 424/449, 483; 216/75, 100, 102

(56) References Cited

U.S. PATENT DOCUMENTS

| | | |
|---|---|---|
| 2,893,392 A | 7/1959 | Wagner et al. |
| 3,034,507 A | 5/1962 | McConnell et al. |

(List continued on next page.)

FOREIGN PATENT DOCUMENTS

| | | | |
|---|---|---|---|
| DE | 19525607 | * | 1/1997 |
| EP | 0497620 | | 8/1992 |
| EP | 0-652 600 | | 11/1994 |
| JP | 7-132119 | | 5/1995 |
| JP | 7132119 A | | 5/1995 |
| JP | 7-196314 | | 8/1995 |
| WO | 93/17754 | | 9/1993 |
| WO | 96/37256 | | 11/1996 |
| WO | 96/40365 | | 12/1996 |
| WO | 96/41236 | | 12/1996 |
| WO | 97/07734 | | 3/1997 |
| WO | 98/00193 | | 1/1998 |
| WO | 98/00194 | | 1/1998 |
| WO | 98/28037 | | 7/1998 |

OTHER PUBLICATIONS

"101 Uses for Tiny Tubules," *Science*247 (1990).
Zuska, "Microtechnology Opens Doors to the Universe of Small Space," *Medical Device and Diagnostic Industry*, p. 131 (Jan. 1997).
"Single–crystal whiskers," *Biophotonics Int'l*, p. 64 (Nov./Dec. 1996).
Edell, et al., "Factors Influencing the Biocompatibility of Insertable Silicon Microshafts in Cerebral Cortex," *IEEE Transactions on Biomedical Engineering*39(6):635–43 (1992).

(List continued on next page.)

*Primary Examiner*—Anhtuan T. Nguyen
(74) *Attorney, Agent, or Firm*—Ropes & Gray

(57) ABSTRACT

Microneedle devices for transport of therapeutic and diagnostic materials and/or energy across tissue barriers, and methods for manufacturing the devices, are provided. The microneedles are hollow and/or porous and have diameters between about 10 nm and 1 mm. The microneedle devices permit drug delivery (or removal or sensing of body fluids) at clinically relevant rates across skin or other tissue barriers, without damage, pain, or irritation to the tissue. Microfabrication techniques are used to cost-effectively produce arrays of microneedles from metals, silicon, silicon dioxide, ceramic, and polymeric materials. Methods are provided for making porous or hollow microneedles.

12 Claims, 3 Drawing Sheets

U.S. PATENT DOCUMENTS

| | | |
|---|---|---|
| 3,086,530 A | 4/1963 | Groom |
| 3,123,212 A | 3/1964 | Taylor et al. |
| 3,136,314 A | 6/1964 | Kravitz |
| RE25,637 E | 9/1964 | Kravitz et al. |
| 3,221,739 A | 12/1965 | Rosenthal |
| 3,221,740 A | 12/1965 | Rosenthal |
| 3,556,080 A | 1/1971 | Hein |
| 3,596,660 A | 8/1971 | Melone |
| 3,675,766 A | 7/1972 | Rosenthal |
| 3,918,449 A | 11/1975 | Pistor |
| 3,964,482 A * | 6/1976 | Gerstel et al. ........... 604/890.1 |
| 4,109,655 A | 8/1978 | Chacornac |
| 4,159,659 A | 7/1979 | Nightingale |
| 4,222,392 A | 9/1980 | Brennan |
| 4,771,660 A | 9/1988 | Yacowitz |
| 4,798,582 A | 1/1989 | Sarath et al. |
| 4,921,475 A | 5/1990 | Sibalis |
| 4,969,468 A | 11/1990 | Byers et al. |
| 5,054,339 A | 10/1991 | Yacowitz |
| 5,138,220 A | 8/1992 | Kirkpatrick et al. |
| 5,250,023 A | 10/1993 | Lee et al. |
| 5,279,544 A | 1/1994 | Gross et al. |
| 5,279,552 A | 1/1994 | Magnet |
| 5,335,670 A | 8/1994 | Fishman |
| 5,364,374 A * | 11/1994 | Morrison et al. ........... 604/272 |
| 5,383,512 A | 1/1995 | Jarvis |
| 5,401,242 A | 3/1995 | Yacowitz |
| 5,457,041 A * | 10/1995 | Ginaven et al. ..... 435/285.1 X |
| 5,527,288 A | 6/1996 | Gross et al. |
| 5,582,184 A | 12/1996 | Erickson et al. |
| 5,591,139 A * | 1/1997 | Lin et al. .................... 604/264 |
| 5,611,806 A | 3/1997 | Jang |
| 5,611,809 A | 3/1997 | Marshall et al. |
| 5,611,942 A * | 3/1997 | Mitsui et al. ................. 216/67 |
| 5,618,295 A | 4/1997 | Min |
| 5,658,515 A | 8/1997 | Lee et al. |
| 5,697,901 A * | 12/1997 | Eriksson ..................... 604/46 |
| 5,801,057 A | 9/1998 | Smart et al. |
| 5,843,114 A | 12/1998 | Jang |
| 5,879,326 A | 3/1999 | Godshall et al. |

OTHER PUBLICATIONS

Frazier, et al., "Two dimensional metallic microelectrode arrays for extracellular stimulation and recording of neurons", *IEEE Proceedings of the Micro Electro Mechanical Systems Conference*, pp. 195–200 (1993).

Haga, et al., "Transdermal iontophoretic delivery of insulin using a photoetched microdevice," *J. Controlled Release* 43:139–49 (1997).

Hashmi, et al., "Genetic Transformation of Nematodes Using Arrays of Micromechanical Piercing Structures," *Bio Techniques* 19(5):766–70 (1995).

Jansen et al., "The Black Silicon Method IV: The Fabrication of Three–Dimensional Structures in Silicon with High Aspect Ratios for Scanning Probe Microscopy and Other Applications," *IEEE Proceedings of Micro Electro Mechanical Systems Conference*, pp. 88–93 (1995).

Lehmann, "Porous Silicon–A New Material for MEMS", *IEEE Proceedings of the Micro Electro Mechanical Systems Conference*, pp. 1–6 (1996).

Reiss, "Glucose—and Blood–Monitoring Systems Vie for Top Spot," *Biophotonics Int'l,* pp. 43–45 (May/Jun. 1997).

Trimmer, et al., "Injection of DNA into Plant and Animal Tissues with Micromechanical Piercing Structures," *IEEE Proceedings of Micro Electro Mechanical Systems Conference*, pp. 111–15 (1995).

* cited by examiner

MICRONEEDLE DEVICE FOR TRANSPORT OF MOLECULES ACROSS TISSUE

STATEMENT REGARDING FEDERALLY SPONSORED RESEARCH

Not applicable.

BACKGROUND OF THE INVENTION

This invention is generally in the field of devices for the transport of therapeutic or biological molecules across tissue barriers, such as for drug delivery.

Numerous drugs and therapeutic agents have been developed in the battle against disease and illness. However, a frequent limitation of these drugs is their delivery: how to transport drugs across biological barriers in the body (e.g., the skin, the oral mucosa, the blood-brain barrier), which normally do not transport drugs at rates that are therapeutically useful.

Drugs are commonly administered orally as pills or capsules. However, many drugs cannot be effectively delivered in this manner, due to degradation in the gastrointestinal tract and/or elimination by the liver. Moreover, some drugs cannot effectively diffuse across the intestinal mucosa. Patient compliance may also be a problem, for example, in therapies requiring that pills be taken at particular intervals over a prolonged time.

Another common technique for delivering drugs across a biological barrier is the use of a needle, such as those used with standard syringes or catheters, to transport drugs across (through) the skin. While effective for this purpose, needles generally cause pain; local damage to the skin at the site of insertion; bleeding, which increases the risk of disease transmission; and a wound sufficiently large to be a site of infection. The withdrawal of bodily fluids, such as for diagnostic purposes, using a conventional needle has these same disadvantages. Needle techniques also generally require administration by one trained in its use. The needle technique also is undesirable for long term, controlled continuous drug delivery.

Similarly, current methods of sampling biological fluids are invasive and suffer from the same disadvantages. For example, needles are not preferred for frequent routine use, such as sampling of a diabetic's blood glucose or delivery of insulin, due to the vascular damage caused by repeated punctures. No alternative methodologies are currently in use. Proposed alternatives to the needle require the use of lasers or heat to create a hole in the skin, which is inconvenient, expensive, or undesirable for repeated use.

An alternative delivery technique is the transdermal patch, which usually relies on diffusion of the drug across the skin. However, this method is not useful for many drugs, due to the poor permeability (i.e. effective barrier properties) of the skin. The rate of diffusion depends in part on the size and hydrophilicity of the drug molecules and the concentration gradient across the stratum corneum. Few drugs have the necessary physiochemical properties to be effectively delivered through the skin by passive diffusion. Iontophoresis, electroporation, ultrasound, and heat (so-called active systems) have been used in an attempt to improve the rate of delivery. While providing varying degrees of enhancement, these techniques are not suitable for all types of drugs, failing to provide the desired level of delivery. In some cases, they are also painful and inconvenient or impractical for continuous controlled drug delivery over a period of hours or days. Attempts have been made to design alternative devices for active transfer of drugs, or analyte to be measured, through the skin.

For example, WO 96/37256 by Silicon Microdevices, Inc. (Godshall) discloses a transdermal drug delivery apparatus that includes a cutter portion having a plurality of microprotrusions, which have straight sidewalls, extending from a substrate that is in communication with a drug reservoir. In operation, the microprotrusions penetrate the skin until limited by a stop region of the substrate and then are moved parallel to the skin to create incisions. Because the microprotrusions are dragged across the skin, the device creates a wound sufficiently large to be a site of infection. Channels in the substrate adjacent to the microprotrusions allow drug from the reservoir to flow to the skin near the area disrupted by the microprotrusions.

U.S. Pat. No. 5,250,023 to Lee et al. discloses a transdermal drug delivery device, which includes a plurality of skin needles having a diameter in the range of 50 to 400 $\mu$m. The skin needles are supported in a water-swellable polymer substrate through which a drug solution permeates to contact the surface of the skin. An electric current is applied to the device to open the pathways created by the skin needles, following their withdrawal from the skin upon swelling of the polymer substrate.

WO 93/17754 by Gross et al. discloses another transdermal drug delivery device that includes a housing having a liquid drug reservoir and a plurality of tubular elements for transporting liquid drug into the skin. The tubular elements may be in the form of hollow needles having inner diameters of less than 1 mm and an outer diameter of 1.0 mm.

While each of these devices has potential use, there remains a need for better drug delivery devices, which make smaller incisions, deliver drug with greater efficiency (greater drug delivery per quantity applied) and less variability of drug administration, and/or are easier to use.

It is therefore an object of the present invention to provide a microneedle device for relatively painless, controlled, safe, convenient transdermal delivery of a variety of drugs.

It is another object of the present invention to provide a microneedle device for controlled sampling of biological fluids in a minimally-invasive, painless, and convenient manner.

SUMMARY OF THE INVENTION

Microneedle devices for transport of therapeutic and biological molecules across tissue barriers, and methods for manufacturing the devices, are provided. The microneedles have diameters between about 10 nm and 1 mm, and preferably are hollow or porous. The microneedle devices permit drug delivery or removal of body fluids at clinically relevant rates across skin or other tissue barriers, with minimal or no damage, pain, or irritation to the tissue.

Microfabrication techniques are used to cost-effectively produce arrays of microneedles from metals, silicon, and polymeric materials. Methods are provided for making porous or hollow microneedles.

For transdermal drug delivery applications, the depth of penetration of the microneedles preferably is in the range of between about 10 $\mu$/m and 100 $\mu$m, so as to penetrate the stratum corneum barrier without penetrating into the dermis, thereby avoiding pain or bleeding, and the diameter of transport pathways created in the skin are preferably less than about 1 $\mu$m, to avoid making a hole which would allow bacteria to enter the penetration wound. The microneedles are also useful for minimally invasive diagnosis of biological fluids. A preferred embodiment of such biosensors is for use in monitoring blood glucose levels, as well as delivery of therapeutics such as insulin.

DETAILED DESCRIPTION OF THE INVENTION

1. Biological Barriers

The devices disclosed herein are useful in transport of material into or across biological barriers including the skin (or parts thereof); the blood-brain barrier; mucosal tissue (e.g., oral, nasal, ocular, vaginal, urethral, gastrointestinal, respiratory); blood vessels; lymphatic vessels; or cell membranes (e.g., for the introduction of material into the interior of a cell or cells). The biological barriers could be in humans or other types of animals, as well as in plants, insects, or other organisms, including bacteria, yeast, fungi, and embryos.

For internal tissues, application of the microneedle devices can be achieved with the aid of a catheter or laparoscope. For certain applications, such as for drug delivery to an internal tissue, the devices can be surgically implanted.

Figure 1:
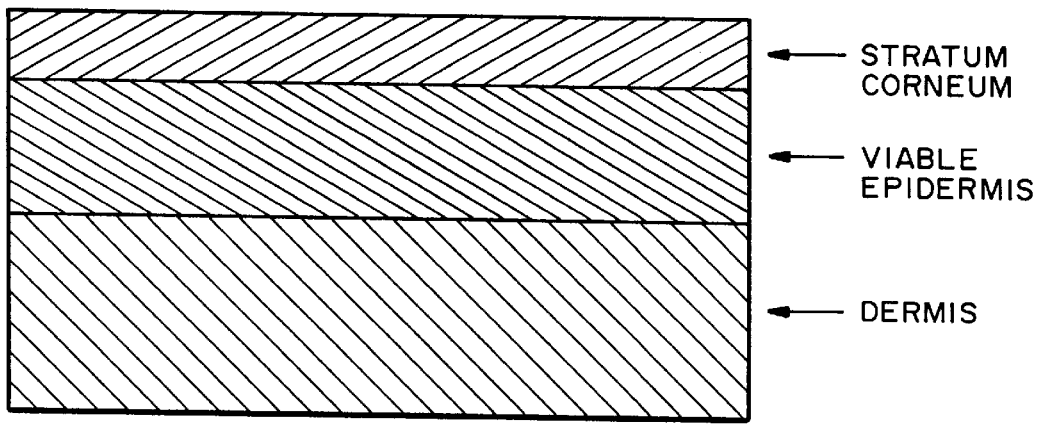
FIG. 1 is a cross-sectional view of human skin.

Skin is a biological barrier of particular use with the microneedle device disclosed herein. A schematic of human skin is shown in FIG. 1. The stratum corneum is the outer layer, generally between 10 and 50 cells, or between 10 and 20 $\mu$/m thick. Unlike other tissue in the body, the stratum corneum contains "cells" (called keratinocytes) filled with bundles of cross-linked keratin and keratohyalin surrounded by an extracellular matrix of lipids. It is this structure that is believed to give skin its barrier properties, which prevents therapeutic transdermal administration of many drugs.

Below the stratum corneum is the viable epidermis, which is between 50 and 100 $\mu$m thick. The viable epidermis contains no blood vessels, and it exchanges metabolites by diffusion to and from the dermis.

Beneath the viable epidermis is the dermis, which is between 1 and 3 mm thick and contains blood vessels, lymphatics, and nerves.

2. The Microneedle Device

The microneedle devices disclosed herein include a substrate; one or more microneedles; and, optionally, a reservoir for delivery of drugs or collection of analyte, a pump(s), sensor(s), and microprocessor(s) to control the interaction of the foregoing.

a. Substrate

The substrate of the device can be constructed from a variety of materials, including metals, ceramics, semiconductors, organics, polymers, and composites. The substrate includes the base to which the microneedles are attached or integrally formed. A reservoir may also be attached to the substrate.

b. Microneedle

The microneedles of the device can be constructed from a variety of materials, including metals, ceramics, semiconductors, organics, polymers, and composites. The microneedles must have the mechanical strength to remain intact and to deliver drugs, or collect biological fluid, while being inserted into the skin, while remaining in place for up to a number of days, and while being removed. The microneedles should be sterilizable using standard methods.

The microneedles can be porous or hollow. As used herein, the term "porous" means having pores or voids throughout at least a portion of the microneedle structure, sufficiently large and sufficiently interconnected to permit passage of fluid and/or solid materials through the microneedle. As used herein, the term "hollow" means having one or more substantially annular bores or channels through the interior of the microneedle structure, having a diameter sufficiently large to permit passage of fluid and/or solid materials through the microneedle. A solid or porous microneedle can be hollow. One of skill in the art can select the appropropriate porosity and/or bore features required for specific applications. For example, one can adjust the pore size or bore diameter to permit passage of the particular material to be transported through the microneedle device.

c. Reservoir

The microneedle device may include a reservoir in communication with the microneedles. In a preferred embodiment, the reservoir contains drug, for delivery through the microneedles. The reservoir may be a hollow vessel, a porous matrix, or a solid form including drug which is transported therefrom. The reservoir can be formed from a variety of materials that are compatible with the drug or biological fluid contained therein. Preferred materials include natural and synthetic polymers, metals, ceramics, semiconductors, organics, and composites.

In a preferred embodiment, the reservoir should be in direct contact with the microneedles and have holes through which drug could exit the reservoir and flow into the interior of hollow or porous microneedles. In another preferred embodiment, the reservoir has holes which permit the drug to transport out of the reservoir and onto the skin surface. From there, drug is transported into the skin, either through hollow or porous microneedles, along the sides of solid microneedles, or through pathways created by microneedles in the skin.

d. Transport Control Components

The microneedle device also must be capable of transporting material across the barrier at a useful rate. For example, the microneedle device must be capable of delivering drug across the skin at a rate sufficient to be therapeutically useful. The device may include a housing with microelectronics and other micromachined structures to control the rate of delivery either according to a preprogrammed schedule or through active interface with the patient, a healthcare professional, or a biosensor. The rate can be controlled by manipulating a variety of factors, including the characteristics of the drug formulation to be delivered (e.g., its viscosity, electric charge, and chemical composition); the dimensions of each microneedle (e.g., its outer diameter and the area of porous or hollow openings); the number of microneedles in the device; the application of a driving force (e.g., a concentration gradient, a voltage gradient, a pressure gradient); and the use of a valve.

The rate also can be controlled by interposing between the drug in the reservoir and the opening(s) at the base end of the microneedle polymeric or other materials selected for their diffusion characteristics. For example, the material composition and layer thickness can be manipulated using methods known in the art to vary the rate of diffusion of the drug of interest through the material, thereby controlling the rate at which the drug flows from the reservoir through the microneedle and into the tissue.

Transportation of molecules through the microneedles can be controlled or monitored using, for example, various combinations of pumps, sensors, actuators, and microprocessors. These components can be produced using standard manufacturing or microfabrication techniques. Actuators that may be useful with the microneedle devices disclosed herein include micropumps, microvalves, and positioners. In a preferred embodiment, a microprocessor is programmed to control a pump or valve, thereby controlling the rate of delivery.

Useful sensors may include sensors of pressure, temperature, chemicals, and/or electromagnetic fields. Biosensors can be located on the microneedle surface, inside a hollow or porous microneedle, or inside a device in communication with the body tissue via the microneedle (solid, hollow, or porous). These microneedle biosensors can include four classes of principal transducers: potentiometric, amperometric, optical, and physiochemical. An amperometric sensor monitors currents generated when electrons are exchanged between a biological system and an electrode. Blood glucose sensors frequently are of this type.

The microneedle may function as a conduit for fluids, solutes, electric charge, light, or other materials. In one embodiment, hollow microneedles can be filled with a substance, such as a gel, that has a sensing functionality associated with it. In an application for sensing based on binding to a substrate or reaction mediated by an enzyme, the substrate or enzyme can be immobilized in the needle interior, which would be especially useful in a porous needle to create an integral needle/sensor.

Wave guides can be incorporated into the microneedle device to direct light to a specific location. Similarly, heat, electricity, or other energy forms may be precisely transmitted to directly stimulate, damage, or heal a specific tissue or intermediary.

Figure 2:
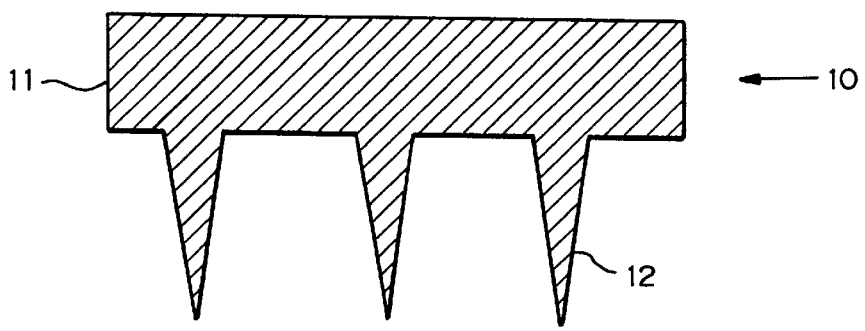
FIG. 2 is a side elevational view of a preferred embodiment of the microneedle device.
Figure 3:
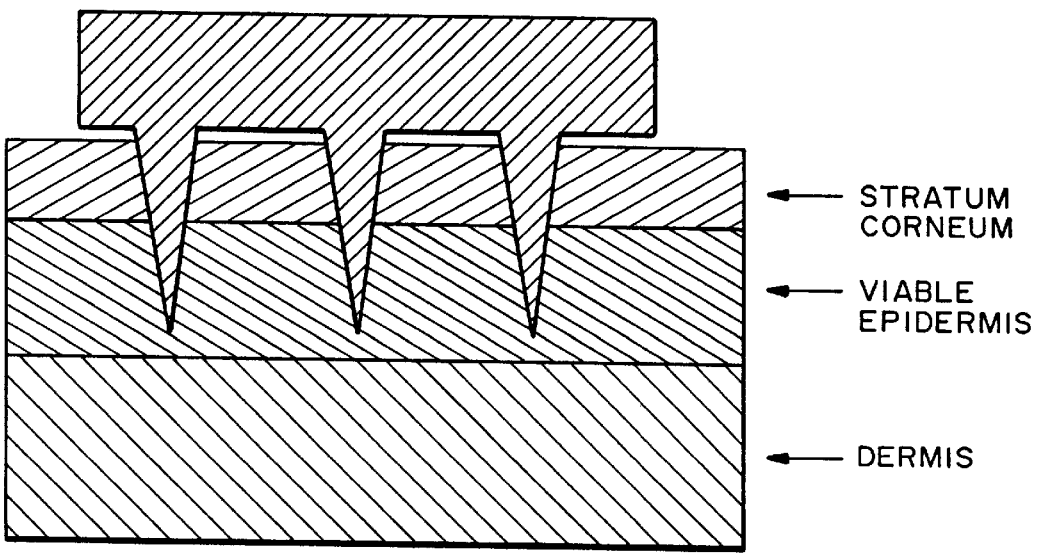
FIG. 3 is a cross-sectional view of a preferred embodiment of the microneedle device applied to human skin.

FIG. 2 is a side elevational view of a schematic of a preferred embodiment of the microneedle device. FIG. 3 is a schematic diagram of the same microneedle device inserted into skin. The device 10 includes an upper portion or substrate 11 from which a plurality of microneedles 12 protrude. The height of the upper portion 11 is between about 1 $\mu$/m and 1 cm, and the width of the upper portion is between about 1 mm and 10 cm. The upper portion 11 of the device can be solid or hollow, and may include multiple compartments. In a preferred embodiment for drug delivery, the upper portion 11 contains one or more drugs to be delivered. It is also preferred that the upper portion include one or more sensors and/or an apparatus (e.g., pump or electrode) to drive (provide/direct the force) transport of the drug or other molecules.

The height (or length) of the microneedles 12 generally is between about 1 $\mu$m and 1 cm. In transdermal applications, the "insertion depth" of the microneedles 12 is preferably less than about 100 $\mu$m, more preferably about 30 $\mu$/m, so that insertion of the microneedles 12 into the skin does not penetrate into the dermis (as described below), thereby avoiding contacting nerves which may cause pain. In such applications, the actual length of the microneedles may be longer, since the portion of the microneedles distal the tip may not be inserted into the skin; the uninserted length depends on the particular device design and configuration. The actual (overall) height or length of microneedles 12 should be equal to the insertion depth plus the uninserted length.

The diameter of each microneedle 12 generally is between about 10 nm and 1 mm, and preferably leaves a residual hole (following microneedle insertion and withdrawal) of less than about 1 $\mu$m, to avoid making a hole which would allow bacteria to enter the penetration wound. The actual microneedle diameter should be larger than 1 $\mu$m, since the hole likely will contract following withdrawal of the microneedle. The diameter of microneedle 12 more preferably is between about 1 $\mu$m and 100 $\mu$m. In a preferred embodiment, the diameter of the microneedle is greatest at the base end of the microneedle and tapers to a point at the end distal the base. Larger diameter and longer microneedles are acceptable, so long as the microneedle can penetrate the biological barrier to the desired depth and the hole remaining in the skin or other tissue following withdrawal of the microneedle is sufficiently small, preferably small enough to exclude bacterial entry. The microneedles 12 can be solid or porous, and can include one or more bores connected to upper portion 11.

3. Methods of Making Microneedle Devices

The microneedle devices are made by microfabrication processes, by creating small mechanical structures in silicon, metal, polymer, and other materials. These microfabrication processes are based on well-established methods used to make integrated circuits and other microelectronic devices, augmented by additional methods developed by workers in the field of micromachining. The microneedle devices can have dimensions as small as a few nanometers and can be mass-produced at low per-unit costs.

a. Microfabrication Processes

Microfabrication processes that may be used in making the microneedles disclosed herein include lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, and lamination. See generally Jaeger, *Introduction to Microelectronic Fabrication* (Addison-Wesley Publishing Co., Reading Mass. 1988); Runyan, et al., Semiconductor Integrated Circuit Processing Technology (Addison-Wesley Publishing Co., Reading Mass. 1990); *Proceedings of the IEEE Micro Electro Mechanical Systems Conference* 1987–1998; Rai-Choudhury, ed., *Handbook of Microlithography. Micromachining & Microfabrication* (SPIE Optical Engineering Press, Bellingham, Wash. 1997). The following methods are preferred for making microneedles.

i. Electrochemical Etching of Silicon

In this method, electrochemical etching of solid silicon to porous silicon is used to create extremely fine (on the order of 0.01 $\mu$m) silicon networks which can be used as piercing structures. This method uses electrolytic anodization of silicon in aqueous hydrofluoric acid, potentially in combination with light, to etch channels into the silicon. By varying the doping concentration of the silicon wafer to be etched, the electrolytic potential during etching, the incident light intensity, and the electrolyte concentration, control over the ultimate pore structure can be achieved. The material not etched (i.e. the silicon remaining) forms the microneedles. This method has been used to produce irregular needle-type structures measuring tens of nanometers in width.

ii. Plasma Etching

This process uses deep plasma etching of silicon to create microneedles with diameters on the order of 0.1 $\mu$m or larger. Needles are patterned directly using photolithography, rather than indirectly by controlling the voltage (as in electrochemical etching), thus providing greater control over the final microneedle geometry.

Figure 4:
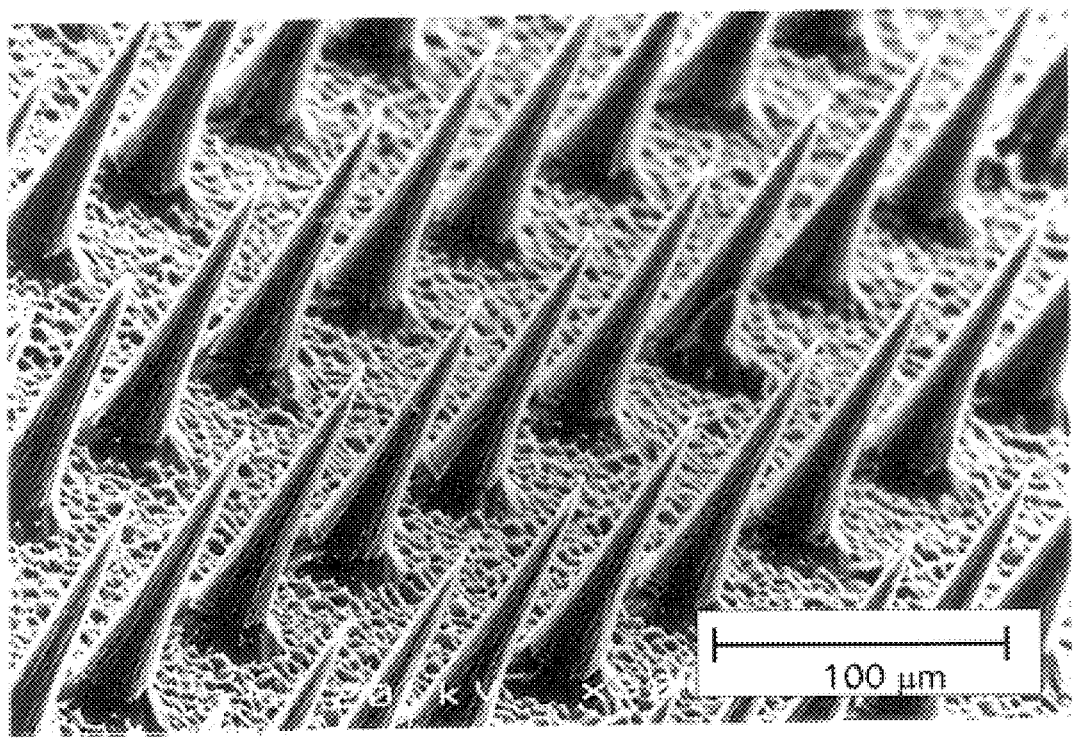
FIG. 4 is a diagram of one embodiment of microneedles.

In this process, an appropriate masking material (e.g., metal) is deposited onto a silicon wafer substrate and patterned into dots having the diameter of the desired microneedles. The wafer is then subjected to a carefully controlled plasma based on fluorine/oxygen chemistries to etch very deep, high aspect ratio trenches into the silicon. See, e.g., Jansen, et al., "The Black Silicon Method IV: The Fabrication of Three-Dimensional Structures in Silicon with High Aspect Ratios for Scanning Probe Microscopy and Other Applications," *IEEE Proceedings of Micro Electro Mechanical Systems Conference*, pp. 88–93 (1995). Those regions protected by the metal mask remain and form the needles. This method is further described in Example 1 below. FIG. 4 provides a diagram of microneedles fabricated by this method.

iii. Electroplating

In this process, a metal layer is first evaporated onto a planar substrate. A layer of photoresist is then deposited onto the metal to form a patterned mold which leaves an exposed-metal region in the shape of needles. By electroplating onto the exposed regions of the metal seed layer, the mold bounded by photoresist can be filled with electroplated material. Finally, the substrate and photoresist mold are removed, leaving the finished microneedle array. The microneedles produced by this process generally have diameters on the order of 1 μm or larger. See, e.g., Frazier, et al., "Two dimensional metallic microelectrode arrays for extracellular stimulation and recording of neurons", *IEEE Proceedings of the Micro Electro Mechanical Systems Conference*, pp. 195–200 (1993).

iv. Other Processes

Another method for forming microneedles made of silicon or other materials is to use microfabrication techniques to make a mold form (A), transferring that mold form to other materials using standard mold transfer techniques, such as embossing or injection molding (B), and reproducing the shape of the original mold form (A) using the newly-created mold (B) to yield the final microneedles (C). Alternatively, the creation of the mold form (A) could be skipped and the mold (B) could be microfabricated directly, which could then be used to create the final microneedles (C).

Another method of forming solid silicon microneedles is by using epitaxial growth on silicon substrates, as is utilized by Containerless Research, Inc. (Evanston, Ill., USA) for its products.

b. Hollow or Porous Microneedles

In a preferred embodiment, microneedles are made with pores or other pathways through which material may be transported. The following descriptions outline representative methods for fabricating either hollow or porous microneedles.

i. Porous Microneedles

Rather than having a single, well-defined hole down the length of the needle, porous needles are filled with a network of channels or pores which allow conduction of fluid or energy through the needle shaft. It has been shown that by appropriate electrochemical oxidation of silicon, pore arrays with high aspect ratios and a range of different pore size regimes can be formed; these pore regimes are defined as (1) microporous regime with average pore dimensions less than 2 nm, (2) mesoporous regime with average pore sizes of between 2 nm and 50 nm, and (3) macroporous regime with pores greater than 50 nm. The mesoporous regime is expected to be most useful for drug delivery. Two approaches to porous needles are generally available, either (a) the silicon wafer is first made porous and then etched as described above to form needles or (b) solid microneedles are etched and then rendered porous by means of electrochemical oxidation, such as by anodization of a silicon substrate in a hydrofluoric acid electrolyte. The size distribution of the etched porous structure is highly dependent on several variables, including doping kind and illumination conditions, as detailed in Lehmann, "Porous Silicon—A New Material for MEMS", *IEEE Proceedings of the Micro Electro Mechanical Systems Conference*, pp. 1–6 (1996).

ii. Hollow Needles

In this approach, one or more distinct and continuous pathways are created through the interior of microneedles. In a preferred embodiment, the microneedle has a single annular pathway along the center axis of the microneedle. This can be achieved by initially chemically or physically etching the holes in the material and then etching away microneedles around the hole. Alternatively, the microneedles and their holes can be made simultaneously or holes can be etched into existing microneedles. As another option, a microneedle form can be made, then coated, and then etched away, leaving only the outer coating to form a hollow microneedle. Coatings can be formed either by deposition of a film or by oxidation of the silicon microneedles to a specific thickness, followed by removal of the interior silicon. Also, holes from the backside of the wafer to the underside of the hollow needles can be created using a front-to-backside infrared alignment followed by etching from the backside of the wafer.

Figure 5A:
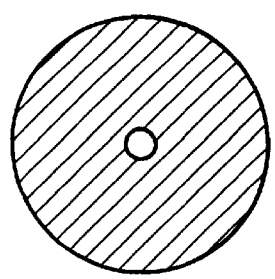
FIGS. 5a and 5b are top and side cross-sectional views, respectively, of a preferred embodiment of a hollow microneedle.
Figure 5B:
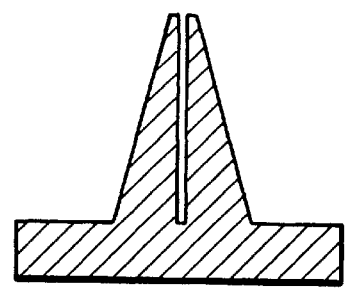

One method for hollow needle fabrication is to replace the solid mask used in the formation of solid needles by a mask that includes a solid shape with one or more interior regions of the solid shape removed. One example is a "donut-shaped" mask. Using this type of mask, interior regions of the needle are etched simultaneously with their side walls. Due to lateral etching of the inner side walls of the needle, this may not produce sufficiently sharp walls. In that case, two plasma etches must be used, one to form the outer walls of the microneedle (i.e., the 'standard' etch), and one to form the inner hollow core (which is an extremely anisotropic etch, such as in inductively-coupled-plasma (ICP) etch). This structure can be achieved by substituting the chromium mask for the solid microneedles by a silicon nitride layer covered with chromium. Solid microneedles are then etched, the chromium is stripped, and the silicon is oxidized. The silicon nitride layer will prevent oxidation at the needle tip. The silicon nitride is then stripped, leaving exposed silicon at the tip of the needle and oxide-covered silicon everywhere else. The needle is then exposed to an ICP plasma which selectively etches the silicon in a highly anisotropic manner to form the interior hole of the needle. FIGS. 5a and 5b illustrate examples of a donut-shaped mask and a microneedle formed thereby, respectively.

A second method uses the solid silicon needles described previously as 'forms' around which the actual needle structures are deposited. After deposition, the forms are etched away, yielding the hollow structures. Silica needles or metal needles can be formed using different methods. Silica needles can be formed by creating needle structures similar to the ICP needles described above prior to the oxidation described above. The wafers are then oxidized to a controlled thickness, forming a layer on the shaft of the needle form which will eventually become the hollow microneedle. The silicon nitride is then stripped and the silicon core selectively etched away (e.g., in a wet alkaline solution) to form a hollow silica microneedle.

Metal needles can be formed by physical vapor deposition of appropriate metal layers on solid needle forms, which can be made of silicon using the techniques described above, or which can be formed using other standard mold techniques such as embossing or injection molding. The metals are selectively removed from the tips of the needles using electropolishing techniques, in which an applied anodic potential in an electrolytic solution will cause dissolution of metals more rapidly at sharp points, due to concentration of electric field lines at the sharp points. Once the underlying silicon needle forms have been exposed at the tips, the silicon is selectively etched away to form hollow metallic needle structures. This process could also be used to make hollow needles made from other materials by depositing a material other than metal on the needle forms and following the procedure described above.

Figure 6A:
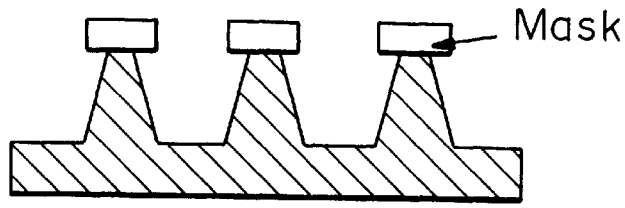
FIGS. 6a through 6d are side cross-sectional views illustrating a preferred method for making hollow microneedles.
Figure 6B:
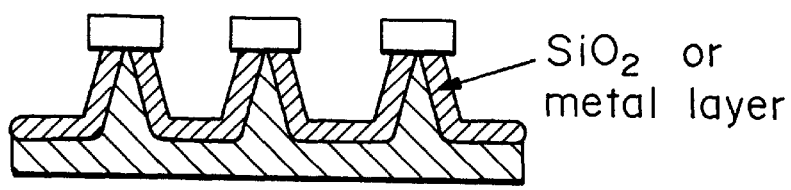
Figure 6C:
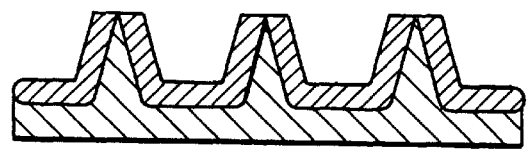
Figure 6D:
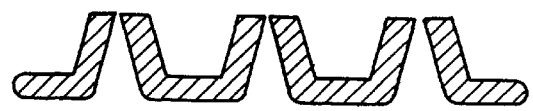

Hollow needles made from silicon dioxide similarly may be made by oxidizing the surface of the silicon needle forms, rather than depositing a metal, and then etching away the solid needle forms and leaving the hollow silicon dioxide structures, as illustrated in FIGS. 6a–6d. FIG. 6a shows an array of needle forms with masks on their tips. In FIG. 6b, the needle forms have been coated with a layer of metal, silicon dioxide or other material. FIG. 6c shows the coated needle forms with the masks removed. Finally, in FIG. 6d, the needle forms have been etched away, leaving hollow needles made of metal, silicon dioxide, or other materials.

In one embodiment, hollow, porous, or solid microneedles are provided with longitudinal grooves or other modifications to the exterior surface of the microneedles. Grooves, for example, should be useful in directing the flow of molecules along the outside of microneedles.

4. Microneedle Device Applications

The device may be used for a single or for multiple uses for rapid transport across a biological barrier or may be left in place for longer times (e.g., days or months) for long-term transport of molecules. Depending on the dimensions of the device, the application site, and the route in which the device is introduced into (or onto) the biological barrier, the device may be used to introduce or remove molecules at specific locations.

As discussed above, FIG. 3 is a side elevational view of a schematic of a preferred embodiment of the microneedle device in a transdermal application. The device 10 is applied to the skin such that the microneedles 12 penetrate through the stratum corneum and enter the viable epidermis so that the tip of the microneedle at least penetrates into the viable epidermis. In a preferred embodiment, drug molecules in a reservoir within the upper portion 11 flow through or around the microneedles and into the viable epidermis, where the drug molecules then diffuse into the dermis for local treatment or for transport through the body.

To control the transport of material out of or into the device through the microneedles, a variety of forces or mechanisms can be employed. These include pressure gradients, concentration gradients, electricity, ultrasound, receptor binding, heat, chemicals, and chemical reactions. Mechanical or other gates in conjunction with the forces and mechanisms described above can be used to selectively control transport of the material.

In particular embodiments, the device should be "user-friendly." For example, in some transdermal applications, affixing the device to the skin should be relatively simple, and not require special skills. This embodiment of a microneedle may include an array of microneedles attached to a housing containing drug in an internal reservoir, wherein the housing has a bioadhesive coating around the microneedles. The patient can remove a peelaway backing to expose an adhesive coating, and then press the device onto a clean part of the skin, leaving it to administer drug over the course of, for example, several days.

a. Drug Delivery

Essentially any drug or other bioactive agents can be delivered using these devices. Drugs can be proteins, enzymes, polysaccharides, polynucleotide molecules, and synthetic organic and inorganic compounds. A preferred drug is insulin. Representative agents include anti-infectives, hormones, and growth regulators. The drug can be for local treatment or for regional or systemic therapy.

In this way, many drugs can be delivered at a variety of therapeutic rates. The rate can be controlled by varying a number of design factors, including the outer diameter of the microneedle, the number and size of pores or channels in each microneedle, the number of microneedles in an array, the magnitude and frequency of application of the force driving the drug through the microneedle and/or the holes created by the microneedles. For example, devices designed to deliver drug at different rates might have more microneedles for more rapid delivery and fewer microneedles for less rapid delivery. As another example, a device designed to deliver drug at a variable rate could vary the driving force (e.g., pressure gradient controlled by a pump) for transport according to a schedule which was pre-programmed or controlled by, for example, the user or his doctor. The devices can be affixed to the skin or other tissue to deliver drugs continuously or intermittently, for durations ranging from a few seconds to several hours or days.

One of skill in the art can measure the rate of drug delivery for particular microneedle devices using in vitro and in vivo methods known in the art. For example, to measure the rate of transdermal drug delivery, human cadaver skin mounted on standard diffusion chambers can be used to predict actual rates. See Hadgraft & Guy, eds., *Transdermal Drug Delivery: Developmental Issues and Research Initiatives* (Marcel Dekker, New York 1989); Bronaugh & Maibach, *Percutaneous Absorption, Mechanisms—Methodology—Drug Delivery* (Marcel Dekker, New York 1989). After filling the compartment on the dermis side of the diffusion chamber with saline, a microneedle array is inserted into the stratum corneum; a drug solution is placed in the reservoir of the microneedle device; and samples of the saline solution are taken over time and assayed to determine the rates of drug transport.

b. Diagnostic Sensing of Body Fluids (Biosensors)

One embodiment of the devices described herein may be used to remove material from the body across a biological barrier, i.e. for minimally invasive diagnostic sensing. For example, fluids can be transported from interstitial fluid in a tissue into a reservoir in the upper portion of the device. The fluid can then be assayed while in the reservoir or the fluid can be removed from the reservoir to be assayed, for diagnostic or other purposes. For example, interstitial fluids can be removed from the epidermis across the stratum corneum to assay for glucose concentration, which should be useful in aiding diabetics in determining their required insulin dose. Other substances or properties that would be desirable to detect include lactate (important for athletes), oxygen, pH, alcohol, tobacco metabolites, and illegal drugs (important for both medical diagnosis and law enforcement).

In one embodiment, one or more microneedle devices can be used for (1) withdrawal of interstitial fluid, (2) assay of the fluid, and (3) delivery of the appropriate amount of a therapeutic agent based on the results of the assay, either automatically or with human intervention. For example, a sensor delivery system may be combined to form, for example, a system which withdraws bodily fluid, measures its glucose content, and delivers an appropriate amount of insulin.

c. Other Applications

The microneedle devices disclosed herein should be useful for penetrating individual cells, for example in gene transfer. See e.g., Hashmi, et al., "Genetic transformation of menatodes using arrays of micromechanical piercing structures," *BioTechniques* 19:766–770 (1995); Trimmer et al., "Injection of DNA into Plant and Animal Tissues with Micromechanical Piercing Structures", *IEEE Proceedings of the Micro Electro Mechanical Systems Conference*, pp. 111–15 (1995).

Other than transport of drugs and biological molecules, the microneedles may be used to transmit or transfer other materials and energy forms, such as light, electricity, heat, or pressure. The microneedles, for example, could be used to direct light to specific locations within the body, in order that the light can directly act on a tissue or on an intermediary, such as light-sensitive molecules in photodynamic therapy.

The microneedle devices disclosed herein also should be useful for controlling transport across tissues other than skin. For example, microneedles could be inserted into the eye across, for example, conjunctiva, sclera, and/or cornea, to facilitate delivery of drugs into the eye. Similarly, microneedles inserted into the eye could facilitate transport of fluid out of the eye, which may be of benefit for treatment of glaucoma. Microneedles may also be inserted into the buccal (oral), nasal, vaginal, or other accessible mucosa to facilitate transport into, out of, or across those tissues. For example, a drug may be delivered across the buccal mucosa for local treatment in the mouth or for systemic uptake and delivery. As another example, microneedle devices may be used internally within the body on, for example the lining of the gastrointestinal tract to facilitate uptake of orally-ingested drugs or the lining of blood vessels to facilitate penetration of drugs into the vessel wall. These uses may involve invasive procedures to introduce the microneedle devices into the body or could involve swallowing, inhaling, injecting or otherwise introducing the devices in a non-invasive or minimally-invasive manner.

EXAMPLE 1

Fabrication of Microneedles

A chromium masking material was deposited onto silicon wafers and patterned into dots having a diameter approximately equal to the base of the desired microneedles. The wafers were then loaded into a reactive ion etcher and subjected to a carefully controlled plasma based on fluorine/oxygen chemistries to etch very deep, high aspect ratio valleys into the silicon. Those regions protected by the metal mask remain and form the microneedles.

<100>-oriented, prime grade, 450–550 $\mu$m thick, 10–15 $\Omega$-cm silicon wafers (Nova Electronic Materials Inc., Richardson, Tex.) were used as the starting material. The wafers were cleaned in a solution of 5 parts by volume deionized water, 1 part 30% hydrogen peroxide, and 1 part 30% ammonium hydroxide (J. T. Baker, Phillipsburg, N.J.) at approximately 80° C. for 15 minutes, and then dried in an oven (Blue M Electric, Watertown, Wis.) at 150° C. for 10 minutes. Approximately 1000 Å of chromium (Mat-Vac Technology, Flagler Beach, Fla.) was deposited onto the wafers using a DC-sputterer (601 Sputtering System, CVC Products, Rochester, N.Y.). The chromium layer was patterned into 20 by 20 arrays of 80 $\mu$m diameter dots with 150 $\mu$m center-to-center spacing using the lithographic process described below.

A layer of photosensitive material (1827 photoresist, Shipley, Marlborough, Mass.) was deposited onto the chromium layer covering the silicon wafers. A standard lithographic mask (Telic, Santa Monica, Calif.) bearing the appropriate dot array pattern was positioned on top of the photoresist layer. The wafer and photoreist were then exposed to ultraviolet (UV) light through the mask by means of an optical mask aligner (Hybralign Series 500, Optical Associates, Inc., Milpitas, Calif.). The exposed photoresist was removed by soaking the wafers in a liquid developer (354 developer, Shipley, Marlborough, Mass.) leaving the desired dot array of photoresist on the chromium layer. Subsequently, the wafers were dipped into a chromium etchant (CR-75; Cyanteck Fremont, Calif.), which etched the chromium that had been exposed during the photolithography step, leaving dot arrays of chromium (covered with photoresist) on the surface of the silicon wafer. The photoresist still present on the chromium dots formed the masks needed for fabrication of the microneedles, described below.

The microneedles were fabricated using a reactive ion etching techniques based on the Black Silicon Method developed at the University of Twente. The patterned wafers were etched in a reactive ion etcher (700 series wafer/batch Plasma Processing System, Plasma Therm, St. Petersburg, Fla.) with means for ensuring good thermal contact between the wafers and the underlying platen (Apiezon N, K. J. Lesker, Clairton, Pa.). The wafers were etched using the following gases and conditions: $SF_6$ (20 standard cubic centimeters per minute) and $O_2$ (15 standard cubic centimeters per minute) at a pressure of 150 mTorr and a power of 150 W for a run time of approximately 250 minutes. These conditions caused both deep vertical etching and slight lateral underetching. By controlling the ratio of flow rates of the $SF_6$ and $O_2$ gases used to form the plasma, the aspect ratio of the microneedles could be adjusted. The regions protected by the chromium masks remained and formed the microneedles. Etching was allowed to proceed until the masks fell off due to underetching, resulting in an array of sharp silicon spikes.

EXAMPLE 2

Transdermal Transport Using Microneedles

To determine if microfabricated microneedles could be used to enhance transdermal drug delivery, arrays of microneedles were made using a deep plasma etching technique. Their ability to penetrate human skin without breaking was tested and the resulting changes in transdermal transport were measured.

Arrays of microneedles were fabricated having extremely sharp tips (radius of curvature less than 1 $\mu$m) which facilitate easy piercing into the skin, and are approximately 150 $\mu$m long. Because the skin surface is not flat due to dermatoglyphics (i.e. tiny wrinkles) and hair, the full length of these microneedles will not penetrate the skin. All experiments were performed at room temperature (23±2° C.).

The ability of the microneedles to pierce skin without breaking was then tested. Insertion of the arrays into skin required only gentle pushing. Inspection by light and electron microscopy showed that more than 95% of microneedles within an array pierced across the stratum corneum of the epidermis samples. Moreover, essentially all of the microneedles that penetrated the epidermis remained intact. On those very few which broke, only the top 5–10 μm was damaged. Microneedle arrays could also be removed without difficulty or additional damage, as well as re-inserted into skin multiple times.

To quantitatively assess the ability of microneedles to increase transdermal transport, calcein permeability of human epidermis with and without inserted microneedle arrays was measured. Calcein crosses skin very poorly under normal circumstances and therefore represents an especially difficult compound to deliver. As expected, passive permeability of calcein across unaltered skin was very low, indicating that the epidermis samples were intact.

Insertion of microneedles into skin was capable of dramatically increasing permeability to calcein. When microneedles were inserted and left embedded in the skin, calcein permeability was increased by more than 1000-fold. Insertion of microneedles for 10 s, followed by their removal, yielded an almost 10,000-fold increase. Finally, insertion of a microneedle array for 1 h, followed by its removal, increased skin permeability by about 25,000-fold. Permeabilities for skin with microneedles inserted and then removed are higher than for skin with microneedles remaining embedded probably because the microneedles themselves or the silicon plate supporting the array may block access to the microscopic holes created in the skin. Light microscopy showed that the holes which remained in the skin after microneedles were removed were approximately 1 μm in size.

To confirm in vitro experiments which showed that skin permeability can be significantly increased by microneedles, studies were conducted with human volunteers. They indicated that microneedles could be easily inserted into the skin of the forearm or hand. Moreover, insertion of microneedle arrays was never reported to be painful, but sometimes elicited a mild "wearing" sensation described as a weak pressure or the feeling of a piece of tape affixed to the skin. Although transport experiments were not performed in vivo, skin electrical resistance was measured before and after microneedle insertion. Microneedles caused a 50-fold drop in skin resistance, a drop similar to that caused by the insertion of a 30-gauge "macroneedle". Inspection of the site immediately after microneedle insertion showed no holes visible by light microscopy. No erythema, edema or other reaction to microneedles was observed over the hours and days which followed. This indicates that microneedle arrays can permeabilize skin in human subjects in a non-painful and safe manner.

Publications cited herein and the material for which they are cited are specifically incorporated by reference.

Those skilled in the art will recognize, or be able to ascertain using on, many equivalents to the specific embodiments of the invention described herein. Such equivalents are following claims.

We claim:

1. A device for transport of material or energy across biological barriers comprising:
   a plurality of hollow microneedles having a length between 100 μm and 1 mm, and
   a substrate to which the microneedles are attached or integrally formed, the microneedles extending at an angle from the substrate,
      wherein the microneedles are made by a microfabrication technique from a material selected from the group consisting of silicon, silicon dioxide, metals, ceramics, and combinations thereof, and
      wherein each microneedle has a shaft, a portion of which comprises one or more substantially annular bores or channels therethrough and which has a width between about 1 μm and 100 μm.

2. The device of claim 1 wherein the microfabrication technique is a micromachining technique selected from the group consisting of lithography, plasma etching, wet chemical etching, dry etching, thermal oxidation of silicon, electroplating, electroless plating, boron diffusion, phosphorus diffusion, arsenic diffusion, antimony diffusion, ion implantation, film deposition, sputtering, chemical vapor deposition, epitaxy, chemical anodization, electrochemical anodization, and combinations thereof.

3. The device of claim 1 wherein the width of the entire shaft of the microneedles is between about 1 μm and 100 μm.

4. The device of claim 1 wherein the length of the microneedles are between about 100 μm and 500 μm.

5. The device of claim 1 wherein the microneedles are in communication with a reservoir.

6. The device of claim 1 wherein the material comprises a metal.

7. The device of claim 1 wherein one or more of the microneedles each comprise a base end which tapers to a sharp tip end, wherein the width of the base end is between about 10 μm and 100 μm.

8. The device of claim 1 wherein the angle is about 90°.

9. The device of claim 6 wherein the material consists essentially of metal.

10. The device of claim 1, wherein the substrate comprises a metal.

11. The device of claim 5, wherein the reservoir contains a drug.

12. The device of claim 11, wherein the drug comprises insulin.

* * * * *